United States Patent [19]

Childers

[11] 4,229,107
[45] Oct. 21, 1980

[54] OPTICAL DENSITOMETER

[75] Inventor: Warren Childers, Houston, Tex.

[73] Assignee: Graphic Arts Manufacturing Company, Houston, Tex.

[21] Appl. No.: 913,680

[22] Filed: Jun. 8, 1978

[51] Int. Cl.³ .................... G01N 21/00; G01J 1/42
[52] U.S. Cl. ...................................... 356/443; 356/223
[58] Field of Search ............... 356/443, 444, 223, 226, 356/227; 250/207; 328/145, 187

[56] References Cited

U.S. PATENT DOCUMENTS 3,765,776  10/1973  Bravenec .................... 356/443 X Primary Examiner—Vincent P. McGraw
Assistant Examiner—Rodney B. Bovernick
Attorney, Agent, or Firm—Bard & Groves

[57] ABSTRACT

In a preferred embodiment of the present invention, method and apparatus are provided for converting an input light intensity representing an optical density to a standard industry scale reading. A photomultiplier tube is operated with a constant anode current corresponding to a reference, or "white" sample, and the dynode voltages varied to obtain the constant anode current. The resulting dynode voltage forms a signal linearly related to the input light intensity. A reference exponential characteristic is selected from an envelope of such characteristics, the selected characteristic cooperating with the photomultiplier tube characteristics. The exponential characteristic envelope may be conveniently formed by resistor-capacitor decay circuits with charging and discharging characteristics compatible with the range of photomultiplier tube parameters to be accommodated, where the envelope curve boundaries cross at a selected reference point. A counter is actuated when the dynode signal voltage equals the decaying exponential characteristic and the counter is disenabled when the exponential characteristic has decayed to a voltage approximating the crossing point of the envelope. The envelope crossing point may be directly detected and used to disenable the counter. The contents of the counter are displayed to present the optical density measurement to a preselected industry scale reading from 0.000 to 4.000.

14 Claims, 6 Drawing Figures

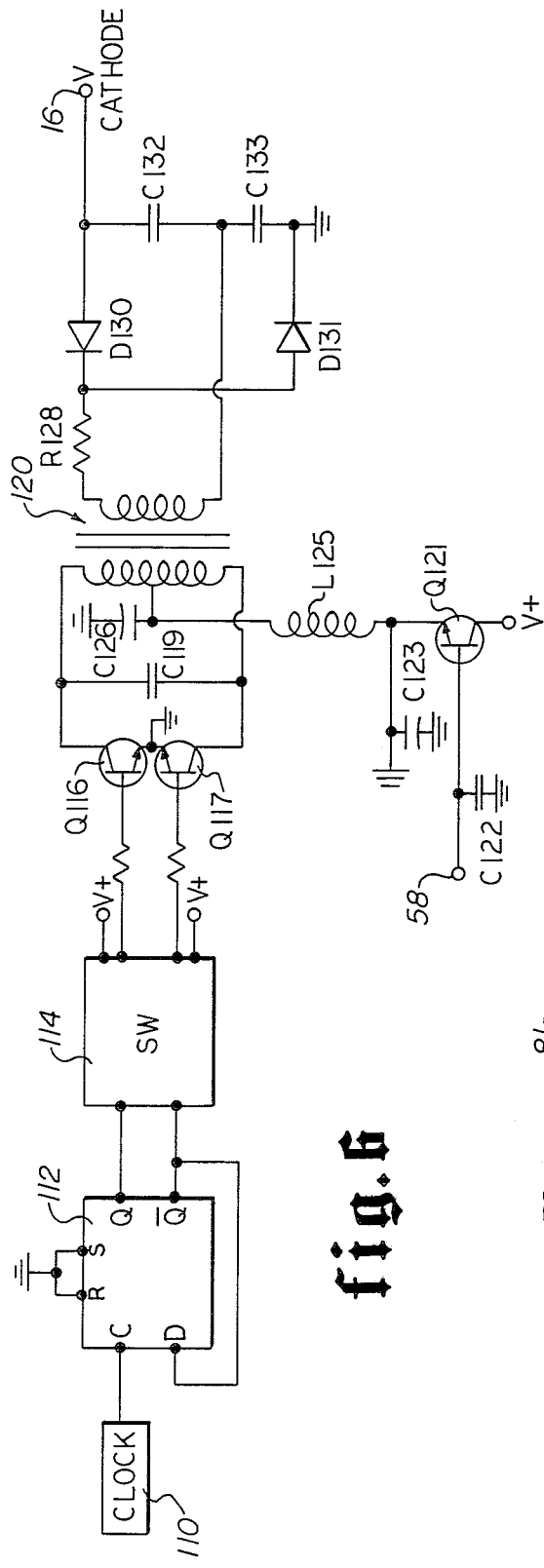
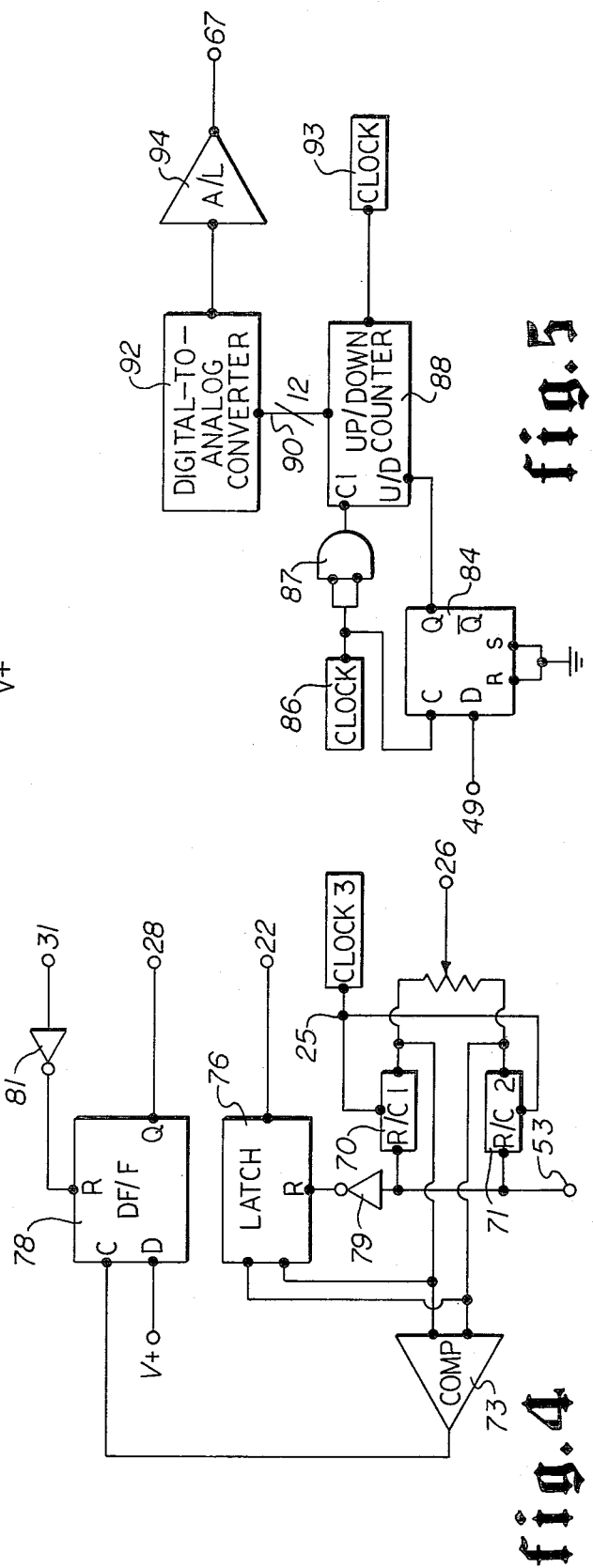
fig. 6
fig. 5
fig. 4

OPTICAL DENSITOMETER

FIELD OF THE INVENTION

This invention relates to optical densitometers generally for use in the photographic industry and, more particularly, to optical densitometers utilizing photomultiplier tubes for converting input light intensities from an optical density sample to an electrical signal.

BACKGROUND OF THE INVENTION

Optical densitometers are in wide use in the graphic arts industry to obtain measurements of relative light intensity reflected from, or transmitted through, a selected surface or portion of a surface. Mesurements may be taken from photographs, photographic negatives, or other image source and the measurements are used to control subsequent photographic exposures. The standard scale in the photographic industry for optical density measurements has a logarithmic base and the present invention includes improved circuitry for converting linear light intensity inputs to the industry standard logarithmic scale.

The standard scale for optical density used in the graphic arts industry is a scale ranging from 0.00 to 4.00. Because of the logarithmic nature of this scale, optical density variations in the range of 1:10,000 may be accommodated. The standard logarithmic scale was developed in the Nineteenth Century when it was discovered that an exponential relationship existed between the mass of metallic silver in a developed photographic negative and the opacity of the negative to light transmission. As the silver mass per unit area increased linearly, opacity increased exponentially. It was also discovered that a linear relationship existed between the opacity of the developed image and the light exposure. Thus, a quantitative determination of the mass of silver present in the developed image provided a measurement of light exposure, the silver mass being logarithmically related to the light exposure.

Electronic instruments are now used to measure optical densities, in lieu of quantitative chemical analyses, but the original scale relationships have been maintained. Thus, "opacity" is still defined as the reciprocal of the percentage light transmission of a given sample and "optical density" is defined as the common logarithm of opacity. Input light intensities may be obtained by either light transmission through a given sample or light reflecting from a sample. The above definitions apply in either situation.

It is conventional to use photomultiplier tubes in electronic optical densitometers for converting input light intensities to electrical signals. The amplification factor of a photomultiplier tube is, among other factors, related to the voltage applied across the dynode system of the photomultiplier tube. The electron flow is increased by the same factor at each dynode so that the final amplification factor may be quite large. Conventional photomultiplier tubes used in the graphic arts industry thus require large voltages for operating the dynode system and obtain anode voltages which may be in the neighborhood of 500–1,000 volts.

In one prior art optical densitometer described in U.S. Pat. No. 3,765,776 to Bravenec, a resistor-capacitor (RC) network is used to provide an exponentially decaying voltage across the dynode system. Thus, the lower the input light intensity, the higher the dynode voltage at which a given anode current is obtained. This feature is used to trigger a counter, initiating a count cycle which terminates when the dynode voltage has discharged to a predetermined level. In this system, maximum dynode voltage is always supplied across the photomultiplier tube. The resulting large voltage swings are detrimental to the photomultiplier tube and to the associated circuit components.

In the prior art, signals generated by the photomultiplier tube in combination with an RC circuit are generally compared with internal reference signals, to produce outputs which may be used to actuate counting apparatus for a time period functionally related to the logarithm of the input light intensity. The need to match the photomultiplier tube and the RC circuit characteristics with internal references has required that photomultiplier tubes for use in optical densitometers have operating characteristics within a very narrow range. The production yield of tubes having such a narrow range of parameters is quite small and it would be very desirable to accommodate a wider range of photomultiplier tube characteristics.

Generally, standard optical density samples are available in the graphic arts industry for calibrating optical densitometers. The basic reference sample is the "white" sample which produces a scale output reading of 0.00. That is, the "white" sample produces a relative light intensity of 1. At the other end of the scale, a "dark" sample produces a relative light intensity of $1 \times 10^{-4}$, or a relative opacity of $1 \times 10^4$.

According to one aspect of the present invention, the operating parameters of the photomultiplier tube are set during an "automatic-zero" cycle where light from a "white" optical density sample is input to the photomultiplier tube. A reference dynode voltage is obtained, the corresponding anode current is determined, and a reference signal is derived corresponding to the anode current. The reference signal is then retained in the optical densitometer to maintain a constant current during a subsequent measurement cycle. In most instances, the reference condition is set using a "white" sample having optical density of 0.00. In this region, it is very desirable to provide increased sensitivity in the automatic zeroing circuitry to obtain an accurate and stable reference anode signal. The disadvantages of the prior art are overcome by the present invention, however, and improved methods and apparatus are provided for obtaining accurate optical density measurements.

SUMMARY OF THE INVENTION

In a preferred embodiment of the present invention, an improved method for converting an input light intensity representing an optical density to a standard industry scale reading is provided, along with an apparatus for measuring optical density. The dynode voltage of a photomultiplier tube is controlled to maintain a constant anode current during a measurement cycle to obtain a dynode voltage functionally related to an input light intensity. The resulting dynode voltage is compared with the voltage from a reference exponential characteristic, which may be a decaying RC circuit, to obtain a first output. The exponential characteristic signal is then compared with a reference signal to obtain a second output. The first output may be conveniently used to start a counter and the second output may conveniently be used to stop a counter, the counter circuit producing a reading according to the industry scale. In one embodiment, improved scale resolution is obtained, the scale output reading from 0.000 to 4.000.

According to one embodiment of the present invention, an RC circuit produces a family of exponential decay curves within a predetermined envelope. An exponential characteristic is selected in cooperation with the photomultiplier tube to produce a reading of 4.000 when exposed to a light intensity from a known 4.000 optical density sample. Any exponential decay characteristic within the envelope may selected, all of the characteristics having a common crossing point.

In another aspect of the present invention, exponential characteristics representing the envelope boundary are detected and the crossing time is detected to obtain the second output. A reliable reference is thus always available.

In yet another aspect of the present invention, the optical densitometer sets the photomultiplier tube operating characteristics when exposed to a known optical density sample, which may generally be a "white" sample. An anode reference current level is detected and an analog reference signal is generated corresponding to the anode current. Exponential circuitry is provided to increase the sensitivity of the analog reference anode signal about the "white" optical density reference sample. The improved resolution in setting the photomultiplier tube operating characteristics particularly cooperates with the improved relationship between the photomultiplier tube and the exponential conversion circuitry to produce an optical densitometer having improved scale resolution.

It is an advantage of the present invention that an increased production yield of photomultiplier tubes can be accommodated.

It is another advantage that large current swings through the photomultiplier tube are minimized and system components are not subjected to extreme high currents on a continuous basis.

Still another advantage is improved stability of the optical density output signal.

Yet another advantage is an increased lifetime for the photomultiplier tube from the constant anode current operation.

Still another advantage of the present invention is that only a single adjustment is required to select a suitable exponential decay characteristic.

It is a feature of the present invention to derive a reference exponential signal from a predetermined envelope of exponential decay curves having a common cross point, the reference exponential signal cooperating with the operating characteristics of a preselected photomultiplier tube to obtain a plurality of predetermined outputs when the photomultiplier tube is exposed to a corresponding plurality of known reference optical densities.

Yet another feature of the present invention is a circuit for generating a reference exponential output having a decay characteristic continuously variable within a preselected envelope, to boundaries of the envelope being selected from the range of photomultiplier tube characteristics to be accommodated, and all of the decay characteristics cross at a common point.

One other feature of the present invention is deriving a reference anode signal during a "zeroing" cycle for controlling anode current during a measurement cycle by deriving adjustments to an analog signal, the adjustments being exponentially related to the difference between the analog signal and the anode current produced by a known reference optical density.

Yet another feature of the present invention is a circuit for providing an analog output signal which is exponentially related to the digital output from a counter.

These and other features and advantages of the present invention will become apparent from the following detailed description, whereas reference is made to the Figures in the accompanying drawings.

IN THE DRAWINGS

FIG. 4 is a schematic depicting an envelope crossing detection and latch circuit.

FIG. 5 is a schematic of an analog reference anode signal generating circuit.

FIG. 6 is a schematic of a DC-DC converter.

DETAILED DESCRIPTION

Figure 1:
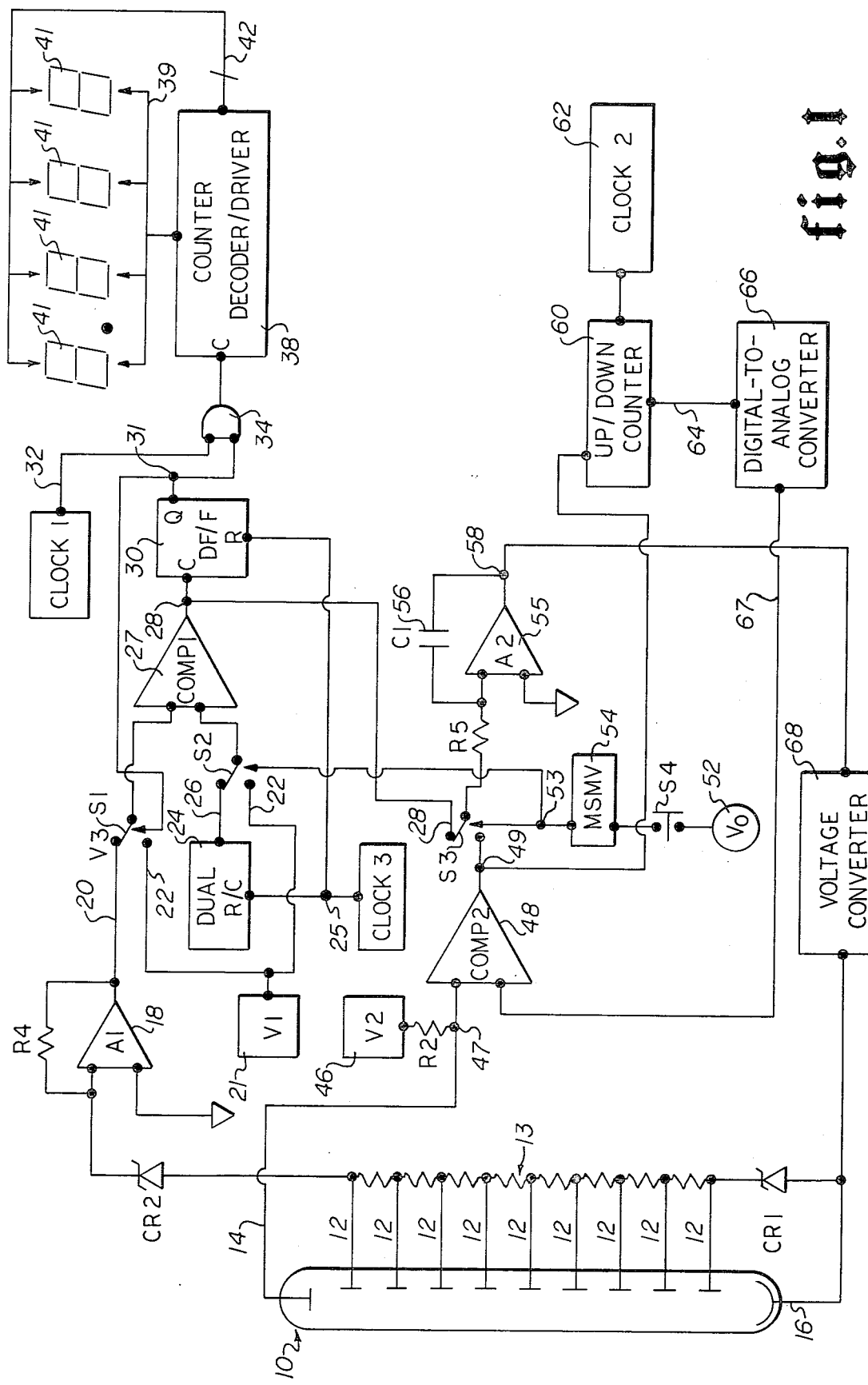
FIG. 1 is a schematic of the optical densitometer according to one embodiment of the present invention.

Referring first to FIG. 1, there may be seen a diagram of one embodiment of the optical densitometer which is the subject of the present invention. Photomultiplier tube 10 serves as the basic input device, and may conveniently receive light from direct exposure or from a light conveyance means such as a fiber optics probe which detects reflected light from an optical density sample to be measured and conveys that light to the photomultiplier tube 10. As hereinafter explained, photomultiplier tube 10 is connected to obtain a constant anode 14 current and the dynode 12 voltage levels are varied to provide an output signal related to the optical density being measured.

In a first mode of operation for setting photomultiplier tube 10 operating parameters, the dynode 12 voltage levels are set to a reference value corresponding to a "white" sample. A white optical density sample is placed beneath the light conveyance means, switch S4 is closed, which may cooperate with a monostable multivibrator 54 to produce control signal 53 which places switch S3 and switch S2 in the "zero-mode" position for adjusting the operating parameters of tube 10. In this condition, switch S3 is connected to receive signal 28 which is the output from a first comparator 27. Switch S2 connects to receive signal 22 which is a first reference voltage V1 and switch S1 is connected to receive the output from amplifier 18.

In the automatic zero-mode condition, the circuit acts to establish operating parameters for photomultiplier tube 10, adjusting voltage V3 to equal reference voltage V1. Reference voltage VI is selected to maintain the dynode 12 collection efficiency over the expected operating range for the dynode 12 voltages. It may be seen from FIG. 1 that V3 is derived from the dynode 12 voltages and is proportional to the dynode voltages. The zener-to-first dynode voltage (about 100 V) and the anode-to-last dynode voltage (about 62 V), are selected to maintain dynamic operation in a linear range. The photomultiplier tube 10 anode current is then linearly related to the dynode 12 voltages for a given light intensity. As hereinafter explained, the circuit will automatically zero with respect to the white sample to produce voltage V3 equal to the reference voltage V1.

Accordingly, voltage V3 and voltage V1 are first applied to comparator 1 which produces an output 28 when V3 and V1 are not equal. Signal 28 is connected by switch S3 to amplifier 55 which has capacitor 56 in a feed back loop, forming an integrating amplifier circuit. Output signal 58 from amplifier 55 then connects to voltage converter 68 which sets the dynode 12 voltages. Thus, integrating amplifier 55 provides an increasing output signal 58 until voltage V3 is equal to V1, thereby maintaining signal 28 at a zero level. Output signal 58 controls voltage converter 68, which provides the high voltage output for the dynodes 12.

While V3 is maintained equal to V1, as hereinabove discussed, a second set of circuits derives an analog signal functionally representing the reference anode operating parameters. The anode 14 current produced by the reference sample is interconnected with voltage source 46, which provides a second reference voltage V2. Voltage V2 may be selected to obtain an increasing anode voltage signal 47 as anode 14 current decreases and may be selected as ground potential. Resistor R2 is selected to provide a convenient voltage level to comparator 48. Thus, a voltage corresponding to the reference anode 14 current is presented to second comparator 48. Control output 49 from comparator 48 is presented to up/down counter 60, which is counting the input pulses from clock 62. A 12 bit digital output 64 is functionally related to the anode 14 current produced by the reference sample.

Converter 66 output signal 67 is then returned to second comparator 48. The up/down counter 60 is controlled by control signal 49 until signal 67 equals signal 47. Thus, comparator 48 controls counter 60 to establish a binary word output from counter 60, which may conveniently be presented in 12 bits, to represent the anode 14 current of the photomultiplier tube 10 at the selected "zero" sample light intensity.

At the completion of the zero-mode operation, the monostable multivibrator 54, if provided in the circuit of the zero-mode selection switch S4, may return to its stable condition, returning switch S2 to conection with signal 26 and switch S3 to connection with signal 49, the output signal from comparator 48. In addition, binary word output 64 of counter 60 is latched to maintain output 67 from converter 66 at a level corresponding to the reference anode 14 current.

The densitometer is now in the measurement mode and a light intensity representing the optical density of a sample to be measured is presented to photomultiplier tube 10. The new light intensity causes a change in anode 14 current. This current change is represented as a change in the voltage 47 presented to comparator 48, which is now comparing anode 14 voltage with reference signal 67, the analog reference anode voltage derived during the auto-zero cycle. Comparator 48 produces an output signal 49 as anode 14 current deviates from the reference condition. Signal 49 is presented to integrator 55 to obtain an integrated output signal 58 for controlling voltage convertor 68. Thus, if a dark sample is being measured, anode 14 current is trying to decrease, resulting in an increased output 58 from integrator 55. Voltage converter 68 acts to increase the voltage across dynodes 12, thereby increasing the current of photomultiplier tube 10 until anode 14 current is returned to a level to produce voltage 47 equal to the reference voltage 67 at comparator 48.

Thus, it may be seen that the optical density sample light intensity manifests itself as an increased current through dynode resistors 13 to obtain increased dynode 12 voltages. The increased current is presented at the input of amplifier 18 and converted to a proportionate increased voltage through resistor R4. Amplifier 18 produces an output signal 20 which is the actual signal voltage V3. Voltage V3 is functionally related to the opacity of the sample and is presented through switch S1 to the first comparator 27. Voltage V3 is a linear relationship with the input light intensity to photomultiplier tube 10 and the system must now convert this signal to the conventional scale for photographic density measurements. As hereinabove explained, the reference measurement system must compress the input signal logarithmically to obtain an output signal on an optical density scale of 0.000 to 4.000, corresponding to a range of relative light intensities from 1 to $1 \times 10^{-4}$ (relative opacity from 1 to $1 \times 10^4$).

It is conventional to obtain this scale conversion using a resistance capacitance (RC) circuit to obtain an exponential reference signal characteristic for comparing against the unknown signal. As hereinbelow explained, a preferred embodiment of the subject densitometer incorporates a new RC circuit 24 which provides discharge characteristics continuously selectable from within an envelope defined by preselected discharge curves. Although the RC circuits are preferred, other electronic circuitry having exponential output characteristics may be used. As further hereinafter explained, all of the exponential reference signal characteristics cross at a common point, which may be conveniently selected to approximate the reference voltage V1.

Figure 2:
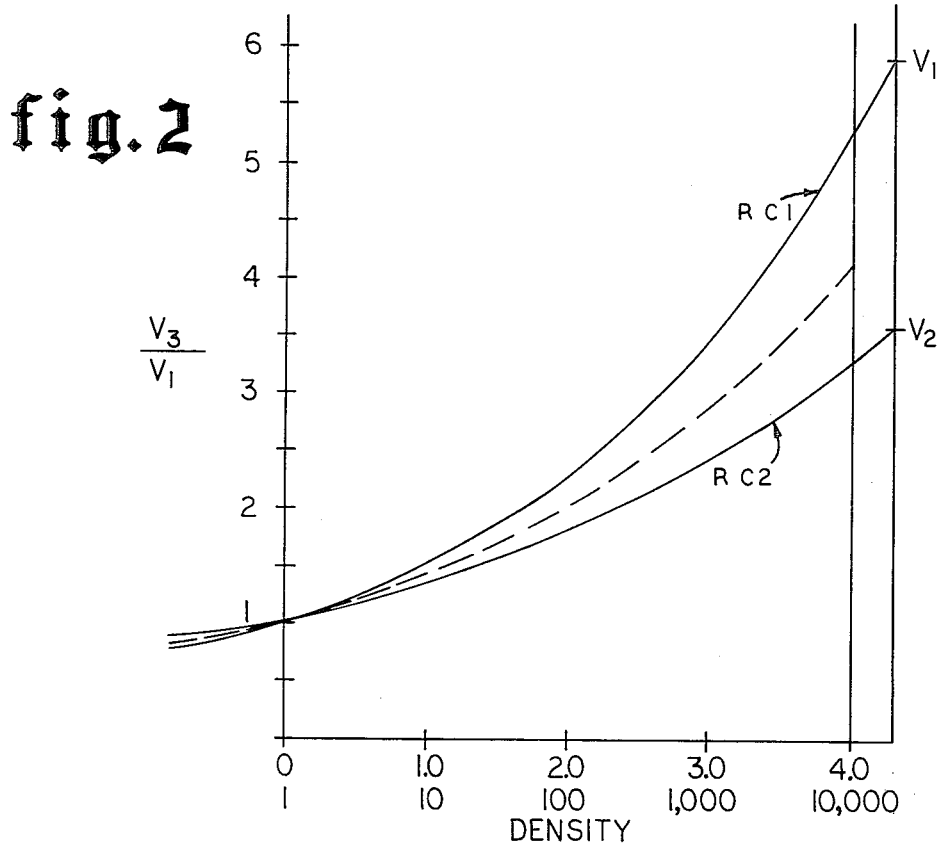
FIG. 2 is a graph showing parameter interrelationships.

The function and operation of the dual RC circuit 24 may be better understood by reference to FIG. 2. The multiplication factor of a given photomultiplier tube 10 is a function of the number of effective dynodes 12 in photomultiplier tube 10. The effective number of dynodes 12 is generally less than the actual number as a result of many variables in tube manufacture. The effect of such changes in tube amplification is to require that a variable logarithmic base be available to convert the light intensity to standard densitometer readings. It can be shown that the effect of the variable exponential output characteristics is to provide a variable base logarithmic-type function to provide an output to the standard industry scale or to other log-base scales, if desired.

As hereinabove explained for the prior art, photomultiplier tubes were selected to obtain a log base which matched the discharge characteristics of a single RC circuit. In the present invention, the exponential characteristics can be widely varied to accommodate a range of multiplication factors which are obtained in a large percentage of a production lot of photomultiplier tubes. Accordingly, changing tube characteristics due to aging effects can be readily accommodated and photomultiplier tubes can be selected without rigid performance specifications.

FIG. 2 generally illustrates the principles hereinabove described. Voltage V3 is functionally related to the dynode voltage which is derived to maintain the anode current at a predetermined reference level when measuring an optical density sample providing light intensity input to a photomultiplier tube having a given amplification factor. Voltage V1 is a reference voltage, hereinbelow discussed, and corresponds to the voltage V3 which would be produced by a white sample, i.e., relative optical density of 0.000. Two RC discharge circuits may be provided, RC1 and RC2, having relative exponential characteristics as shown in FIG. 2. The upper envelope boundary RC1 charges to a voltage V1 and has a decay constant T1. The lower envelope boundary RC2 charges to a voltage V2, which is less than V1, and has a decay constant T2 greater than T1.

The exponential decay characteristics of RC1 and RC2 are determined by the values for (V1, T1) and (V2, T2), respectively. These values are selected to accommodate a selected range of amplification factors obtained from an acceptable yield of photomultiplier tubes as manufactured. As hereinbelow described, a potentiometer interconnecting the two RC circuits permits an output exponential characteristic to be selected which falls anywhere within the evelope determined by RC1 and RC2.

Another design constraint for the RC1 and RC2 circuits is that the envelope boundary characteristics cross at a level which approximates the reference voltage V1. Where a separate voltage source is used to obtain V1, circuit components may have to be adjusted to obtain this capability. Alternately, the actual crossing point may be measured and used directly for the reference voltage.

The exponential characteristic appropriate for a given photomultiplier tube is set initially using industry standard optical density samples. This is done by exposing the standard sample to the input probe and adjusting the exponential characteristics until the desired output reading is obtained. Adjustment need only be done infrequently, since tube characteristics change only slowly, or if the photomultiplier tube must be replaced.

Thus, in operation, the capacitors in the RC circuits are charged to V1 and V2, as hereinabove discussed. As the sample measurement cycle begins, voltage V3 is compared with the selected exponential characteristic output voltage and counter 38 is enabled to begin counting when the two voltages become equal. The counter continues to count as the RC circuit voltages decay, the selected exponential characteristic voltage now being compared with the reference voltage V1. When the reference voltage V1 and the exponential characteristic voltage become equal, counter 38 is disenabled and the results may be displayed. Thus, it may be seen that the displayed results correspond to the measured optical density and converted to a standard densitometer scale output.

Figure 3:
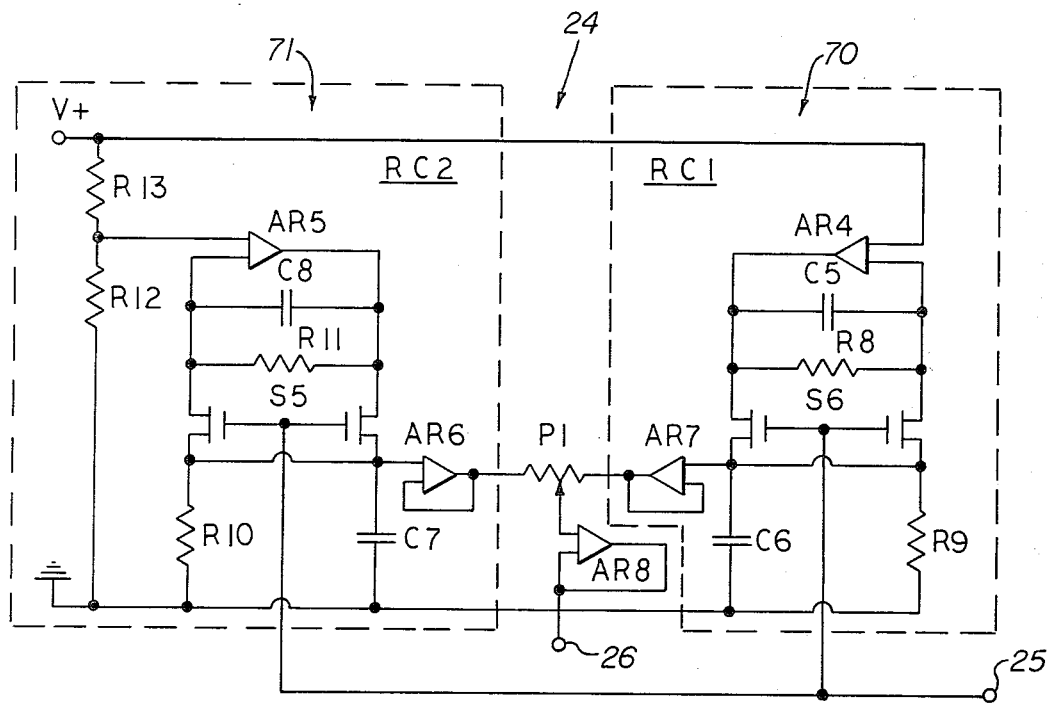
FIG. 3 is a detailed schematic of the preferred embodiment of the reference exponential characteristic circuit.

Referring now to FIG. 3, there is more particularly depicted a preferred embodiment of an actual circuit for the dual RC circuit 24 shown in FIG. 1. Each RC circuit, RC1 and RC2, operates in a substantially identical manner, and the operation of RC1 will be briefly described. A voltage source V+ is provided to charge RC1 to V1 during the display clock cycle determined by clock 3 (see FIG. 1). Amplifier AR4 acts to enable rapid charging of the capacitor during the display cycle. The application of control signal 25 from clock 3 (FIG. 1) actuates switch S6 to disconnect the circuit from AR4 causing discharge of capacitor C6 through resistor R9. The decaying voltage is presented through amplifier AR7 to a potentiometer P1 which, in conjunction with the decaying voltage from circuit RC2 determines the voltage decay curve presented to amplifier AR8 as the selected exponential characteristic output signal 26. Only a single adjustment, potentiometer P1 is adjusted to obtain the desired exponential characteristic, as hereinabove discussed. Resistor R9 in RC1 and resistor R10 in RC2 may be selected to obtain the decay curve envelope hereinabove discussed. Typical component values for the circuit depicted in FIG. 3 are presented in Table 1.

TABLE 1

| V+ | 11.7V | C7 | 1µF |
| R8 | 1 M | C8 | .01 |
| R9 | 40.2K 1% | P1 | 100K |
| R10 | 49.9K 1% | AR4 | LM358 |
| R11 | 1 M | AR5 | LM358 |
| R12 | 26.1K 1% | AR7 | CA3140S |
| R13 | 10.0K 1% | AR7 | CA3140S |
| C5 | .01 | AR8 | CA3140S |
| C6 | 1µF | S5 | CD4016 |
|  |  | S6 | CD4016 |

Referring now to FIG. 4, there may be seen a logical diagram for circuitry to determine a reference voltage V1 from the actual crossing of the two exponential characteristic envelope boundary curves. It is desirable to use the actual crossing point for improved accuracy since slight drifts in circuit parameters occur and some difference may develop between the actual crossing point and a fixed V1 reference voltage. A logical signal may be obtained when the decay voltages are equal and such a logical signal applied to disenable counter 38 at the time of the crossing, which may conveniently be done by blocking the input 32 from clock 1 (see FIG. 1). It is more difficult to integrate the automatic zero feature with this feature since an actual voltage output must be derived for comparison with input voltage V3.

FIG. 4 depicts one embodiment of logic circuitry for obtaining an internally generated reference voltage V1. In order to obtain the signal needed to disenable counter 38, the voltage outputs from RC1 70 and RC2 71 are separately presented to comparator 73. An output from comparator 73 is obtained when the two inputs are equal, i.e., the time the decay curves intersect, and this output signal 74 is presented to flip-flop 78. A high Q output is obtained which may be applied as signal 28 to flip-flip 30 (see FIG. 1) to reset the output of flip-flop 30 to a low Q signal 31. As shown in FIG. 1, a low Q signal 31 disenables AND gate 34 and interrupts the pulse train to counter 38. Low Q output 31 may also be applied through NOT gate 81 to reset flip-flop 78 for the next crossing signal. Signal 28 thus indicates the event of decay curve crossing and not the actual value of voltage at the crossing in order to disenable counter 38 and display the contents of counter 38, representing the optical density of the measured sample.

For use in an automatic-zero mode, signal 53 from the automatic-zero mode switch S4 is provided to cause RC1 70 and RC2 71 to begin a discharge cycle. The voltage outputs from each RC circuit are separately presented to a voltage follower and latch circuit 76 which determines the voltage at the crossing point and displays that voltage as signal 22, which is now reference voltage V1 at switch S2 in FIG. 1. The reference voltage V1 thus generated is used as described in FIG. 1 to set the reference system operating parameters.

The voltage follower and latch circuit 76 as depicted in FIG. 4 may be formed in a variety of ways. One convenient circuit design would be the circuit hereinbelow discussed in the description of FIG. 5 for the analog reference anode signal generator. Converting the voltage outputs from RC1 70 and RC2 72 to digital outputs for direct comparison may be easily accomplished using conventional integrated circuitry. The digital signal at the time of signal equality may be detected and transferred to a register for retention and conversion to a suitable analog signal representing reference voltage V1 throughout the automatic-zero cycle.

Referring now to FIG. 5, there may be seen a schematic of an analog reference anode signal generator, used to generate the reference anode voltage and depicted in FIG. 1 as counter 60, clock 62, and digital-to-analog converter 66. An input signal 49 is provided to flip-flop 84, signal 49 representing the relative magnitudes of output 67 and the reference anode 14 voltage, as shown in FIG. 1. Signal 49 will result in a high Q output from flip-flop 84 on the occurrence of a clock pulse from clock 86. For example, if the anode voltage 47 is greater than output 67 from the analog reference anode signal generator, comparator 48 (FIG. 1) will produce an output signal 49 resulting in a high Q output from flip-flop 84 which is applied as control signal 49 to the up/down control of counter 88. The presence of a signal 49 may typically cause counter 84 to count up.

Pulses from clock 86 are transferred to counter 88 through AND gate 87 causing a 12 bit binary word to appear at the output of counter 88. This 12 bit binary word 90 will move up and down about some mean value as analog reference anode signal generator output 67 is continuously compared with the anode voltage 47.

Binary word 90 is then presented to digital-to-analog converter 92 to obtain an analog output functionally related to the actual anode current produced during the zeroing cycle. In general, the reference condition uses a white sample as the reference optical density. To accommodate a linear scale factor of 1:1×10⁴, however, it is very desirable to have expanded scale resolution about the reference, or "1", point. Accordingly, the output from converter 92 is presented to antilogarithmic amplifier 94. Now, output 67 is functionally related to the antilogarithm of counter 88 output and the improved "zero" resolution has been obtained. Suitable circuit components are shown in TABLE 2.

TABLE 2

| FF84 | CD4013 |
|---|---|
| Counter 88 | CD4029 |
| D/A Converter 92 | Burr-Brown DAC-80 |
| Anti Log.Amp. 94 | Analog Devices No. 755 |

Thus, a closed loop is presented, continuously comparing the analog reference anode signal output 67 with the reference anode 14 voltage. A steady state condition is never quite achieved, but output 67 will oscillate slightly about the desired reference voltage. When clock 86 is disenabled, counter 88 retains the last 12 bit binary word as output signal 90, thereby latching output signal 67 at the desired analog reference anode signal level for use during the measurement portion of the instrument cycle.

As hereinabove explained, the anode current is maintained at a reference level throughout the measurement cycle by controlling dynode voltage until the anode current returns to its reference value. A photomultiplier tube 10 requires high voltage to operate, while the various system logic components use relatively low DC voltages. Accordingly, low DC control voltages must be converted to high voltage for photomultiplier tube 10 operation, and FIG. 6 depicts a preferred embodiment of a DC voltage controlled DC voltage converter 68, as depicted in FIG. 1.

Basically, the voltage converter circuit 68 is composed of a clock 110 which triggers flip-flop 112 to drive a switching circuit 114. Switching circuit 114 controls transistors Q116 and Q117 to drive transformer 120. Thus, an oscillating voltage is produced across the primary coils of transformer 120. The magnitude of this oscillating voltage is determined by the input of transformer 120. Thus, the primary voltage swing, and hence the secondary voltage swing, is determined by input control signal 58.

In one embodiment, the primary-to-secondary turns ratio of transformer 120 is 520/14,000, whereby a high voltage output is produced. The secondary of transformer 120 is connected to a conventional voltage doubler and filter circuit comprised of diodes D130 and D131, and capacitors C132 and C133. Thus, a DC output voltage is obtained at a level sufficient to operate photomultiplier tube 10 and controlled by low level DC voltage 58. Typically, output voltages in the range of 360–1400 VDC may be controlled by voltages in the range 3–14 VDC. Typical circuit components are listed in TABLE 3.

TABLE 3

| FF112 | CD4013 | C126 | 2.2/20μF |
|---|---|---|---|
| SW 114 | CD4016 | C132 | .01μF/1KV |
| Q116 | 2N1711 | C133 | .01μF/1KV |
| Q117 | 2N1711 | T120 | 520/14,000 |
| Q121 | 2N1711 | L125 | 27μH |
| C119 | .01μF | R128 | 10K |
| C122 | .01μF | D130 | MR250-2 |
| C123 | 2.2/20μF | D131 | MR250-2 |

Referring again to FIG. 1, it may be seen that decoder/driver 38 presents the output to a resolution of 0.001. Prior art optical densitometers have heretofore resolved the measurement to only 0.01. Improved resolution is provided according to one embodiment of the present invention because of the combination of the selectable exponential characteristic and the high resolution from the automatic zero setting circuit. The automatic zero circuit resolution obtains a stable and relatively insensitive analog reference anode signal for use during subsequent sample measurements. Then, the matching capability provided by the variable exponential characteristic obtains increased accuracy using the 0.001 resolution at the output.

It is therefore apparent that the present invention is one well adapted to attain all of the features and advantages hereinabove set forth, together with other advantages which will become obvious and inherent from a description of the preferred embodiment. It will be understood that certain combinations and subcombinations are of utility and may be employed without reference to other features and subcombinations. This is contemplated by and is within the scope of the present invention.

What is claimed is:
1. A method for measuring the optical density of a photographic sample, including steps of
generating a signal envelope defining exponential curves decaying toward a common crossing point;
selecting from within said envelope a reference exponential signal cooperating with the operating characteristics of a preselected photomultiplier tube to obtain a plurality of predetermined outputs when said photomultiplier tube is exposed to a plurality of known reference optical densities;

exposing said photomultiplier tube to an optical density to be measured;

deriving a dynode signal voltage for said photomultiplier tube to maintain an anode current through said photomultiplier tube at a preset reference condition during said exposure to said optical density to be measured; and deriving an optical density output signal funtionally related to the time for said reference exponential signal to decay from a high level functionally related to said dynode signal voltage to a low level functionally related to a first known reference optical density.

2. The method according to claim 1, wherein deriving said reference exponential signal includes:

deriving a first exponential signal forming a first envelope boundary, deriving a second exponential signal forming a second envelope boundary and crossing said first exponential boundary;

applying said first and second exponential signals across a potentiometer, and deriving a reference exponential signal from said potentiometer to obtain a predetermined output when said photomultiplier tube is exposed to a known optical density.

3. The method according to Claim 1 or claim 2, including the step of deriving said low level from said common crossing point of said exponential decay curves.

4. The method according to claim 1, wherein deriving an optical density output signal comprises the steps of:

comparing said reference exponential signal with said dynode signal voltage, enabling a counter to count an incoming pulse train when said reference exponential signal is equal to said dynode signal voltage, and disenabling said counter when said reference exponential signal reaches said low level.

5. The method according to claim 4, further including the steps of comparing first and second exponential decay curves forming said predetermined envelope to detect said common crossing point, deriving said low level functionally related to said common crossing point to disenable said counter when said crossing occurs.

6. In an optical densitometer having a photomultiplier tube for amplifying an input light intensity, an exponential conversion circuit for converting the output from said photomultiplier tube to a signal functionally related to an industry standard scale and means for deriving an output signal from said converted signal, an improved exponential conversion circuit comprising:

means for generating a reference exponential output signal having a decay characteristic continuously variable within a preselected envelope, the boundaries of said envelope being selected for utilizing photomultiplier tubes having a known range of amplification factors, all of said decay characteristics decaying toward a common crossing point.

7. Apparatus according to claim 6, including: first exponential signal means for generating an upper boundary of said preselected envelope, second exponential signal means for generating a lower boundary of said preselected envelope and crossing said upper boundary at said common crossing point, and means interconnecting said first and second exponential signal means for deriving said reference exponential output signal.

8. Apparatus according to claim 7, wherein: said first exponential signal means including a first resistor-capacitor circuit chargeable to a first voltage and having a first decay time constant, said second exponential signal means including a second resistor-capacitor circuit chargeable to a second voltage and having a second decay time constant, and said first voltage being greater than said second voltage and said first time constant being less than said second time constant to obtain said common crossing point at a voltage approximating a reference voltage functionally related to an output signal from said photomultiplier tube when exposed to a reference optical density for white.

9. Apparatus according to claim 7 or claim 8, further including:

first switch means for enabling a counter when said reference exponential output signal is equal to an output from said photomultiplier tube functionally related to an optical density to be measured, and second switch means for disenabling said counter when said reference exponential output signal equals said common crossing point.

10. Apparatus according to claim 9, wherein said second switch means includes:

comparator means for producing an output when the output from said first exponential signal means equals the output from said second exponential signal means, gate means for blocking clock pulses to said counter upon receiving said output from said comparator.

11. An optical densitometer using a photomultiplier tube to measure the optical density of a photographic sample, comprising:

means for generating a signal envelope defining exponential curves decaying toward a common crossing point;

means for selecting from within said envelope a reference exponential signal cooperating with the operating characteristics of said photomultiplier tube to obtain a plurality of predetermined outputs when said photomultiplier tube is exposed to a plurality of known reference optical densities;

means for exposing said photomultiplier tube to an optical density to be measured;

means for deriving a dynode signal voltage for said photomultiplier tube to maintain an anode current through said photomultiplier tube at a preset reference condition during said exposure to said optical density to be measured; and means for deriving an optical density output signal functionally related to the time for said reference exponential signal to decay from a high level functionally related to said dynode signal to a low level functionally related to a first known reference optical density.

12. Apparatus according to claim 11, wherein said means for deriving said reference exponential signal includes:

means for deriving a first exponential signal forming a first envelope boundary, means for deriving a second exponential signal forming a second envelope boundary and crossing said first exponential boundary, a potentiometer interconecting said first and second exponential signals, and means for deriving a reference exponential signal from said potentiometer to obtain a predetermined output when said photomultiplier tube is exposed to a known optical density.

13. Apparatus according to claim 11 or claim 12, wherein said means for deriving an optical density output signal comprises:

means for comparing said reference exponential signal with said dynode signal voltage, means for enabling a counter to count an incoming pulse train when said reference exponential signal is equal to said dynode signal voltage, and means for disenabling said counter when said reference exponential signal reaches said low level signal.

14. Apparatus according to claim 13, wherein said means for disenabling said counter includes:

comparator means for comparing first and second exponential decay curves forming said predetermined envelope to detect said common crossing point and produce an output, and gate means for blocking said pulse train to said counter upon receiving said output from said comparator means.

* * * * *